US005756067A

United States Patent [19]
Redgrave et al.

[11] Patent Number: 5,756,067
[45] Date of Patent: May 26, 1998

[54] LABELLED DIAGNOSTIC COMPOSITIONS AND METHOD OF THEIR USE

[75] Inventors: Trevor G. Redgrave; Ian J. Martins, both of Nedlands, Australia

[73] Assignee: Peptide Delivery Systems Pty Ltd, Subiaco, Australia

[21] Appl. No.: 648,080

[22] PCT Filed: Oct. 28, 1994

[86] PCT No.: PCT/AU94/00663

§ 371 Date: May 8, 1996

§ 102(e) Date: May 8, 1996

[87] PCT Pub. No.: WO95/13096

PCT Pub. Date: May 18, 1995

[30] Foreign Application Priority Data

Nov. 8, 1993 [AU] Australia ................... PM2286

[51] Int. Cl.$^6$ .................... A61K 51/00; A61M 36/14
[52] U.S. Cl. .................... 424/1.81; 424/1.11; 424/1.65
[58] Field of Search .................... 424/1.11, 1.65, 424/1.69, 1.81, 9.1, 9.2; 436/71; 552/544

[56] References Cited

U.S. PATENT DOCUMENTS

| | | | |
|---|---|---|---|
| 3,894,844 | 7/1975 | Pinto et al. | 436/71 |
| 4,039,285 | 8/1977 | Teipel | 436/71 |
| 4,676,974 | 6/1987 | Hofmann et al. | 424/9.1 |
| 4,753,788 | 6/1988 | Gamble | 424/1.11 |
| 4,772,549 | 9/1988 | Frossard | 435/6 |
| 4,933,157 | 6/1990 | Counsell et al. | 424/1.11 |
| 4,938,947 | 7/1990 | Nicolau | |
| 5,135,848 | 8/1992 | Abel et al. | 435/7.21 |
| 5,320,968 | 6/1994 | Seman | 436/71 |
| 5,362,649 | 11/1994 | Schwertner | 436/71 |
| 5,432,058 | 7/1995 | Lange, III et al. | 424/1.11 |
| 5,496,735 | 3/1996 | Schwertner | 436/71 |

FOREIGN PATENT DOCUMENTS

| | | |
|---|---|---|
| 0028917 | 5/1981 | European Pat. Off. |
| 0084439 | 7/1983 | European Pat. Off. |
| 0182131 | 5/1986 | European Pat. Off. |
| 0190050 | 8/1986 | European Pat. Off. |
| 204137 | 9/1986 | Japan. |
| WO8607540 | 12/1986 | WIPO. |
| 9110128 | 7/1991 | WIPO. |
| WO9320800 | 10/1993 | WIPO. |
| 9513096 | 5/1995 | WIPO. |

OTHER PUBLICATIONS

Mortimer et al (1995), Journal of Biological Chemistry, vol. 270 Nov. 48, pp. 28767–28776, Intracellular Localization and Metabolism of Chylomicron Remnants in the Livers of Low Density Lipoprotein Receptor–deficient Mice and ApoE–deficient Mice.

Redgrave et al (1995), Journal of Lipid Research, vol. 36, pp. 2670–2675, "Measurement of Expired Carbon Dioxide to Assess the Metabolism of Remnant Lipoproteins".

Oliveira et al (1988), Biochimica et Biophysica Acta, vol. 958, pp. 211–217, "Competition Between Chylomicrons and Their Remnants for Plasma Removal: A Study with Artificial Emulsion Models of Chylomicrons".

Lenzo et al (1988), Biochimica et Biophysica Acta, vol. 960, pp. 111–118, "Effects of Phospholipid Composition on the Metabolism of Triacylglycerol, Cholesteryl Ester and Phosphatidyl Choline from Lipid Emulsions Injected Intravenously in Rats".

*Primary Examiner*—John Kight
*Assistant Examiner*—Dameron Jones
*Attorney, Agent, or Firm*—Fredrikson & Byron, P.A.

[57] ABSTRACT

This invention relates to a labelled diagnostic composition for testing presence of or propensity for atherosclerosis and coronary artery disease and the like comprising components which mimic essential features of an exogenous lipoprotein transport particle, said composition being capable of metabolisation by normal physiological pathways such that at least one labelled metabolite is detectable in the blood or bodily waste of a patient being tested. Furthermore, it also relates to a method of determining the presence of or propensity for atherosclerosis or coronary artery disease and the like in a patient requiring such determination comprising administering to said patient a labelled diagnostic composition which mimics essential features of an exogenous lipoprotein transport particle, and measuring the quantity of labelled metabolite in the bodily waste or blood of said patient so as to determine the quantity of labelled diagnostic composition successfully metabolised by said patient.

12 Claims, 2 Drawing Sheets

LABELLED DIAGNOSTIC COMPOSITIONS AND METHOD OF THEIR USE

This invention relates to formulations useful in the diagnosis of a patient's predisposition to the development of atherosclerosis and coronary artery disease. It also relates to a method of diagnosing a patient's tendency to develop such diseases.

The predisposition of a person to develop atherosclerosis is dependent on several factors including genetic inheritance and environment. Atherosclerosis is a progressive disease of the walls of blood vessels, beginning with the accumulation of lipid substances and over a period of years leading to pathological changes such as fibrosis, ulceration and thrombosis within the vessel wall. Serious diseases consequent upon atherosclerosis include myocardial infarction, aneurysm, stroke and failure of adequate blood supply to organs and limbs leading to organ failure and gangrene. The disease is very common in Western countries where a diet high in cholesterol, excessive fat ingestion, cigarette smoking, obesity and physical inactivity are all contributing factors. Genetic factors can also lead to onset of atherosclerosis.

Although methods such as angiography and measurements of blood flow currently exist for assessment of established atherosclerosis, there are no current, accurate tests available to determine the likelihood that a patient has a metabolic predisposition towards development of the disease. Since treatments are available and preventative behavioural changes possible, such a method of predetermining a propensity to develop atherosclerosis would be useful to both patient and physician.

Tests currently available to measure the risk of developing atherosclerosis include measuring the plasma contents of cholesterol, triglycerides and lipoproteins. However it is clear that these tests are not conclusive since approximately one-half of heart disease due to atherosclerosis occurs in patients with plasma triglycerides and cholesterol within the normal range of the population. Moreover, angiographic evidence of atherosclerosis has been documented in patients having normal lipid levels.

One such test is described in Australian Patent Application 66416/90 to LEHIGH UNIVERSITY. In this patent application a patients propensity for atherosclerosis is measured by the number of low density lipoprotein receptors in the blood sample. Specifically, the rate of low density lipoprotein and receptor internalisation, and the rate of synthesis of receptors is measured by fluorescent assay.

An alternative method is described in Australian Patent Application 71429/91 to THE BETH ISRAEL HOSPITAL FOUNDATION. This patent application discloses a method for predicting atherosclerotic risk by the NMR measurement of protein resonance of high density lipoproteins compared to that of healthy individuals.

One particle not measured in current tests is chylomicrons which transport fat in the form of triacylglycerols from the small intestine to fat depots. The triglycerides in these particles are subject to a hydrolysis action by lipoprotein lipases in the bloodstream resulting in formation of a secondary particle which still contains up to 30% triglycerides, and the whole of the particle cholesteryl ester. This secondary particle is known as a chylomicron remnant or chyloremnant. The chyloremnant, having been divested of much of its triglyceride content, then contains a much higher relative amount of cholesterol to phospholipid. The primary function of the chyloremnant is to transport cholesterol from the intestine to the liver.

There is now evidence to suggest that an individuals ability to metabolise chyloremnants may be directly related to their propensity to develop atherosclerosis, and thus measurement of chyloremnants, or their precursor particles, chylomicrons is desirable as a diagnostic tool for atherosclerosis and related diseases. A reduced tolerance for chyloremnant clearance would indicate increased risk of atherosclerosis, while repeated tolerance tests would be useful in judging the effectiveness of therapies and interventions aimed at reducing atherosclerosis risk.

Such measurement is relatively difficult. The metabolism of chylomicrons is very rapid, in particular, the half-life of intact chylomicrons in the blood stream is estimated at about 4.5 minutes. Furthermore, in the plasma, recognition and measurement of chylomicrons is difficult owing firstly to the fact that the amount of chylomicrons is low in relation to other lipoproteins, and secondly because the composition of chylomicrons is not unique except, sometimes, for the presence of apolipoprotein-B48. Neither flotation in an ultracentrifuge nor size exclusion chromatography separate chyloremnants from chylomicrons because of overlaps in the sizes and the densities of the particles and their precursors.

There have been several attempts to measure a patients capacity to handle chyloremnants circulating in their system. In one attempt, it was found that apolipoprotein-B48 is secreted into chylomicrons from the small intestine, and thus this was used as a specific probe to assess the presence of chyloremnants in the bloodstream. The ratio of apolipoprotein -B48 to apolipoprotein -B100 found in low density lipoproteins was used to show a higher post-prandial content in chyloremnant containing fractions of plasma in patients with coronary artery disease compared with controls. (Simons et al (1979) *Chylomicrons and chylomicron remnants in coronary artery disease: a case-control study* Atherosclerosis 65, 181–189).

Another attempt measured changes in plasma triglycerides in post-prandial plasma during steady intestinal delivery of fat to measure chylomicron triglyceride clearance in man, but this gave no information about chyloremnant clearance. (Grundy and Mok (1976) *Chylomicron clearance in normal and hyperlipaedemic man.* Metabolism 25, 1225–1239).

Still others have measured levels of protein, cholesterol, cholesteryl esters and retinyl esters in the bloodstream.

These methods generally require extensive sampling of blood, extensive processing of blood samples and complex analytical chemistries to obtain an assessment of the clearance of exogenous lipid and lipoprotein levels. Furthermore, and importantly, the current methods are insensitive to small changes in a patients capacity to metabolise exogenous particles. Small changes are important to identify because atherosclerosis in some individuals may be due to small changes over a period of many years.

Existing methods of measuring chylomicrons or chyloremnants are also difficult to interpret for theoretical reasons because they only measure changes in the steady concentration of substance in plasma, whereas because the removal process of chyloremnants is very rapid, in many individuals clearance is achieved with minimal change in the overall concentration in the blood.

Accordingly it is an object of this invention to provide a diagnostic formulation and diagnostic method for the simple, readily available clinical analysis of an individuals likelihood of developing atherosclerosis and coronary artery disease.

Figure 1:
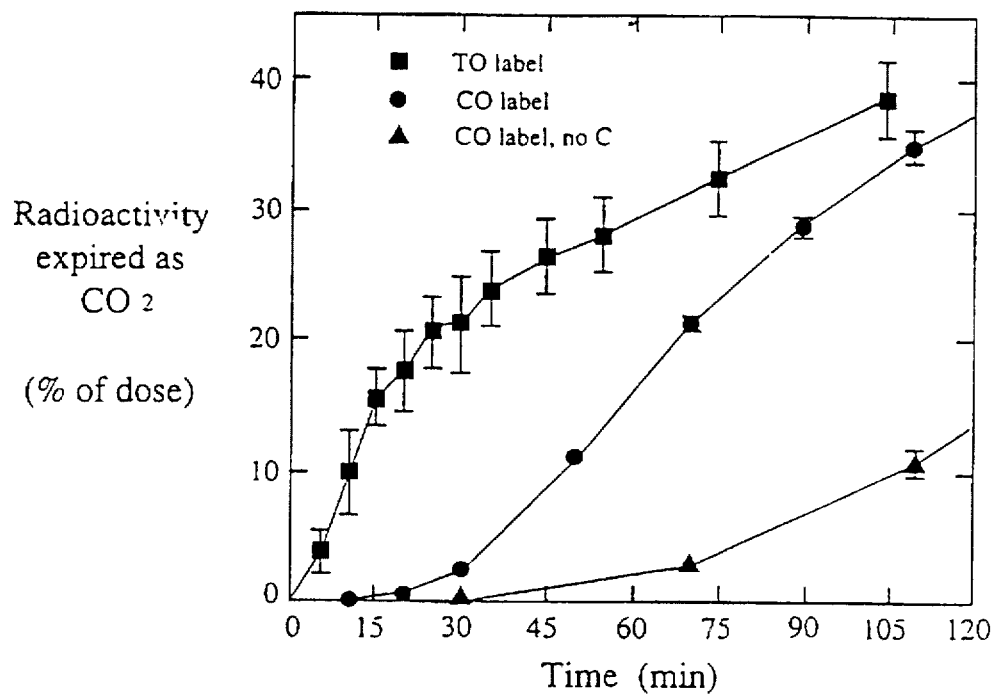
FIG. 1 shows a plot "Radioactivity expired as $CO_2$" vs. "Time", as described in Example 1.

To this end there is provided in a first aspect of the invention a labelled diagnostic composition for testing presence of or propensity for atherosclerosis and coronary artery disease and the like comprising components which mimic essential features of an exogenous lipoprotein transport particle, said composition being capable of metabolisation by normal physiological pathways such that at least one labelled metabolite is detectable in the blood or bodily waste of a patient being tested.

This invention is predicated on the discovery that the measurement of a labelled metabolite derived from a suitable mimic of the body's exogenous lipoprotein transport system which has been artificially introduced into a patient to be tested constitutes a directly proportionate measurement of that patients level of development, or predisposition to the development of atherosclerosis.

In a preferred form of this invention, the labelled diagnostic composition is one which mimics the chemical formulation of a chyloremnant, that is, it is preferably one which is primarily lipidic in nature. The composition should preferably be one that results in no untoward local or systemic reaction following introduction to the patient being tested, and should, preferably be well tolerated by the patient upon repeated administration.

In particular, it is preferred that the labelled diagnostic composition comprises particles of a diameter from 20–2000 nanometers. Size is a determinant of metabolism, and to this extent, it is preferred that the particles be of a size that it is easily metabolised. Most desirably, the size of the particles is in the range 35–200 nanometers, and most preferably, a diameter of about: 150 nm.

For ease and accuracy of quantitive measurement of the patient's propensity to develop atherosclerosis, the labelled metabolite may be measured in the captured expired air of the patient, although it is also envisaged that it will be possible to measure a patients propensity for atherosclerosis from samples of urine, or blood.

Desirably, the composition according to this aspect of the invention includes triglycerides, phospholipids, cholesterol, and cholesteryl esters, at least one of these having a suitably located label. Preferably the composition is in the form of an emulsion for intravenous injection although other administration routes may be possible. If, for example, the composition is to be administered orally, it should be suitably formulated so as to be resistant to gastric degradation.

Preferably, the label is located on the cholesteryl ester so as to ensure that it is properly distributed between the other constituents of the composition. However, compounds other than cholesteryl esters may be used provided that they behave as do cholesteryl esters. Suitable compounds may include vitamin A derivatives and non-endogenous xenobiotics. In a preferred aspect of the invention, the label is attached to the fatty acid moiety of the cholesteryl ester. Other chemistries of attaching the label to the cholesteryl ester are also possible.

The components of the composition, including the labelled component are preferably emulsified in a solution in water of glycerol and salts, for example sodium chloride and buffer salts. The presence of the glycerol improves the stability in storage of the composition and makes it isotonic. The composition may additionally include a small quantity of an anti-oxidant to preserve the lipids against oxidation. Such anti-oxidants as ascorbic acid or vitamin E are suitable. To stably emulsify the composition, well known techniques such as sonication or microfluidization may be used. Emulsion particle size affects the kinetics of clearance, so it is desirable that the emulsion preparation procedures result in particles of the preferred size as set out hereinabove.

Cholesteryl esters, preferably present in an amount of 0.5–30% of total lipids, which are suitable for use in the composition of the invention include cholesteryl oleate, cholesteryl linoleate or a mixture of related esters. Cholesteryl esters are generally the carrier of the label which enables measurement of the metabolisation of the compositions according to the invention. The fatty acid moiety of the cholesteryl ester is preferably that labelled.

In this last respect, radiolabelling, such as with $^{14}C$ or other equivalent, physiologically tolerated radioactive isotopes is possible. Also possible is the use of a label allowing the measurement of the amount of metabolite present by mass spectrometry. For example, $^{13}C$ may be used so that the isotope enrichment ratio of $^{13}C$ relative to $^{12}C$ in the $CO_2$ of the expired breath of a patient can be measured. Other equivalent, physiologically tolerated, stable, non-radioactive isotopes, tritium or other labels could also be incorporated into the composition.

Triglycerides, which may be present in the composition in an amount of 20–95% of total lipids, and which are suitable for use in the composition include triolein, soybean oil, safflower oil, or other suitable substitutes such as olive oil or corn oil triglycerides.

Suitable phospholipids include egg yolk phosphatidylcholine, soybean phosphatidylcholine, dioleoyl phosphatidylcholine, or other suitable substitutes. This lipid may be present in an amount of 5–50% of total lipids.

Cholesterol which should be present in amounts adequate for the metabolism of the composition to mimic that of the natural exogenous lipid transport particles, is preferably present in amounts of 0.5–30% of total lipids. Without cholesterol it has been found that the chyloremnants remain in the plasma for much longer than occurs physiologically, and thus a composition not having cholesterol is not able to properly mimic the natural exogenous lipid transport particles and is therefore not entirely suitable for the purposes of the invention.

In a preferred diagnostic composition according to the invention there is present 1–15% cholesteryl ester, 30–90% triglycerides, 8–30% phospholipids and 1–15% cholesterol.

In one preferred composition according to the invention, there is present approximately 84% triolein, 4% cholesteryl oleate, 2% cholesterol and 10% egg phosphatidylcholine.

In total, the lipid content of the composition is preferably present in amounts of 1–50% of the total aqueous-based emulsion.

In a second aspect of the invention there is provided a method of determining the presence of or propensity for atherosclerosis and coronary artery disease and the like in a patient requiring such determination comprising administering to said patient a labelled diagnostic composition which mimics essential features of an exogenous lipoprotein transport particle, and measuring the quantity of labelled metabolite in the bodily waste or blood of said patient so as to determine the quantity of labelled diagnostic composition successfully metabolised by said patient.

Although this method may be used to ascertain the level of development of atherosclerosis by a patient, because chyloremnant metabolism may vary from person to person, the method is also useful for gauging over an interval of repeated tests, a patient's decline towards an atherosclerotic state.

Most desirably, the composition mimicking the essential features of the exogenous lipoprotein particle is delivered to the patient by injection.

In a preferred embodiment of this aspect of the invention said labelled diagnostic composition is one which mimics the chemical formulation of a chyloremnant, that is, it is primarily lipidic in nature.

For optimum analysis, the measurement of the quantity of labelled metabolite present in the blood or bodily waste of the individual is measured from the patient's expired air, and is preferably carried out at intervals over a period of several hours. Measurements of the quantity of labelled metabolite may commence as early as 15 minutes after inoculation of the patient with the compositions according to the invention, and may be concluded as long as six hours or more after the initial administration of the composition to the patient.

The individuals expired air may be collected in a known fashion by trapping the expelled air in a vessel containing solutions which trap $CO_2$ created as a result of the individuals metabolism.

Whilst the labelled diagnostic composition is preferably administered as an emulsion by intravenous injection, it may also be administered by a suitable alternative route such as orally.

A preferred composition administered in accordance with this aspect of the invention includes 20–95% by weight of total lipids of triglycerides, 5–50% by weight of total lipids of phospholipids, 0.5–30% by weight of total lipids of cholesterol, and 0.5–30% by weight of total lipids of cholesteryl esters, at least a small proportion of which may be labelled.

Suitable cholesteryl esters, triglycerides, phospholipids and sources of cholesterol are as previously described.

In one preferred method according to the invention, the labelled diagnostic composition comprises 1–15% cholesteryl ester, 30–90% triglycerides, 8–30% phospholipids and 1–15% cholesterol.

A preferred aspect of the invention illustrating both the composition according to the invention and the method of the invention will now be described with reference to the two following examples.

EXAMPLE 1

Emulsions were prepared by sonication and purified by density gradient centrifugation. The emulsions contained cholesteryl 1-$^{14}$C oleate or glycerol tri-1-$^{14}$C-oleate to label the cholesteryl oleate or triolein constituents respectively. recipient rats were prepared under barbiturate anaesthesia with a cannula in a jugular vein for making intravenous injections. After awakening from the anaesthetic, the rat was placed in a closed chamber through which a stream of room air was passed. Experiments were commenced by injection of labelled emulsion intravenously, and to trap $CO_2$ the air leaving the chamber was passed through solutions containing 0.21 mol/L phenethylamine (Aldrich, Milwaukee, Wis.), 50 ml of Permafluor Packard, Downers Grove, Ill.), 270 ml of methanol and 410 ml of toluene. Aliquots of the solution were than counted by liquid scintillation spectrometry.

Emulsions containing 83.4±0.4% triolein, 4.1±0.46% cholesteryl oleate (radioactively labelled with $^{13}$C), 1.4±0.04% cholesterol and 11.1±0.46% egg phosphatidylcholine were injected intravenously into rats and the amounts of radioactive $CO_2$ in the expired breath were measured over several hours subsequently. As shown in FIG. 1, label in the triolein (TO) triglyceride portion of the emulsion appeared rapidly in the expired breath, with approximately 20% expired in 30 minutes. Triolein triglycerides are not metabolised via the same route as is the cholesteryl ester component of the emulsion. With cholesteryl ester (CO), only a few percent of radioactivity appeared in the expired breath in the first 30 minutes, but by 90 minutes approximately 30% of the radioactivity had been expired. To confirm the essential requirement of cholesterol, the experiment was repeated with CO label in an emulsion without cholesterol (FIG. 1, no C). By 90 minutes after injection, less than 10% of the emulsion radioactivity had appeared in the expired breath, in contrast to the standard emulsion, containing cholesterol, where approximately 30% of radioactivity had appeared by 90 minutes.

EXAMPLE 2

Figure 2:
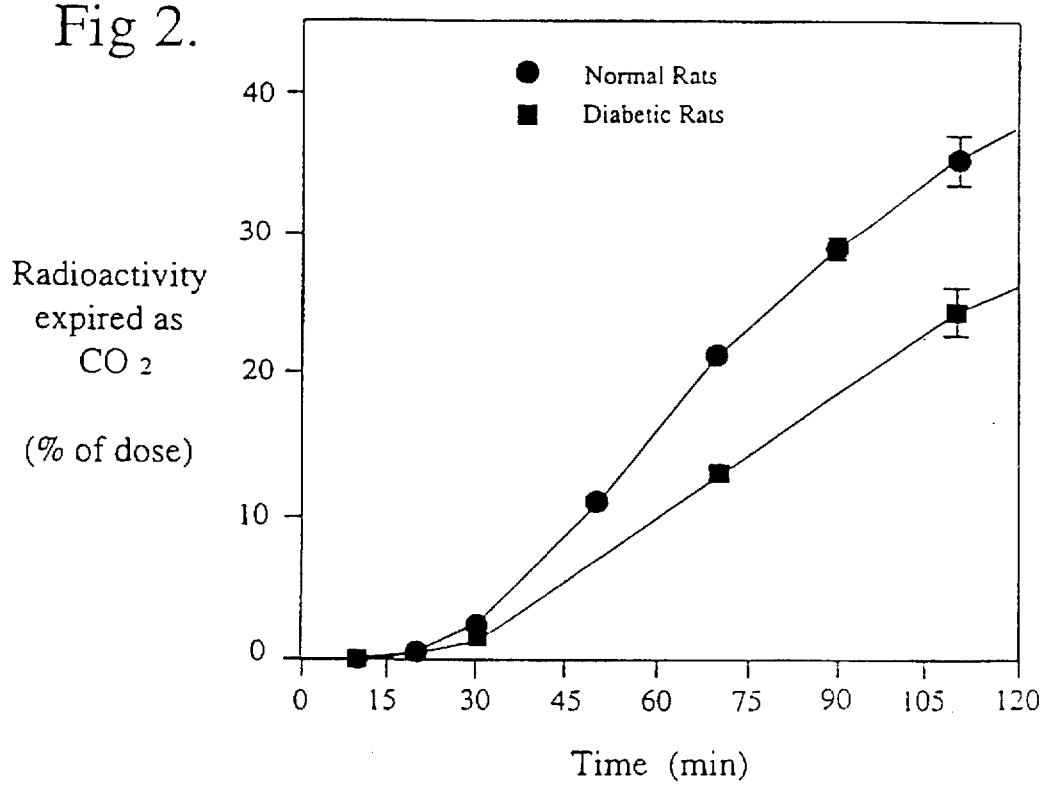
FIG. 2 shows a plot of "Radioactivity expired as $CO_2$" vs. "Time", as described in Example 2.

To test the suitability of the compositions of the invention as a diagnostic test for the presence of conditions predisposing to atherosclerosis, the CO labelled emulsion was injected into rats three weeks after they were treated with streptozotocin at a dose of 50 mg/kg given intravenously to render them diabetic. Rats made diabetic in this way have been shown to have defective clearance of chyloremnants from plasma (Redgrave et al, 1990, *The effect of insulin deficiency on the metabolism of lipid emulsion models of triacylglycerol-rich lipoproteins in rats* Metabolism; 39:1–10). Three weeks after the treatment with streptozotocin the concentration of blood glucose was increased and glucosuria was present. Plasma lipids were only slightly increased. Emulsions were prepared by sonication and purified by density gradient centrifugation as before. Cholesteryl 1-$^{14}$C-oleate was present to label the emulsion CO component. Recipient rats were prepared as described above and placed in a closed chamber for collection of expired breath after intravenous injection of labelled emulsion. FIG. 2 shows that the expired radioactivity was decreased in the diabetic rats compared with the non-diabetic controls, illustrating the ability of the invention to detect and diagnose a defect in the ability of the individual recipient to metabolize chyloremnants. It is apparent from an examination of FIG. 2 that the rate of expiration of the radioactive $CO_2$ was slower in diabetic rats than in similarly studied normally control rats. Compared with approximately 30% expiration of the label in normal rats, diabetic rats expired only about 20% of the injected dose after 90 minutes. The results are means±SEM from 3 rats in each group.

This difference illustrates the ability of the invention to detect the change in atherosclerosis predisposition associated with diseases, for example, diabetes.

EXAMPLE 3

In Watanabe Heritable Hyperlipidaemic Rabbits (WHHL), low density lipoprotein receptors are defective. Consequently the clearance of low density lipoproteins is slow and the concentration of low density lipoproteins in the plasma is increased, leading to the development of atherosclerosis. Furthermore, the clearance of remnants of the triglyceride-rich lipoproteins is defective in WHHL, a reflection of the role of low density lipoprotein receptors acting as a ligand for apoliprotein E associated with remnants.

Heterozygous WHHL are obtained by cross breeding half-lop rabbits with homozygous WHHL, and animals from the half-lop strain are used as controls. Emulsions were prepared by sonication and purified by density gradient centrifugation as before. Cholesteryl-$^{14}$C-oleate was present to label the emulsion cholesteryl oleate component. Rabbits were placed in a closed chamber for collection of expired breath after intravenous injection of labelled emulsion as previously described for the studies in rats.

Figure 3:
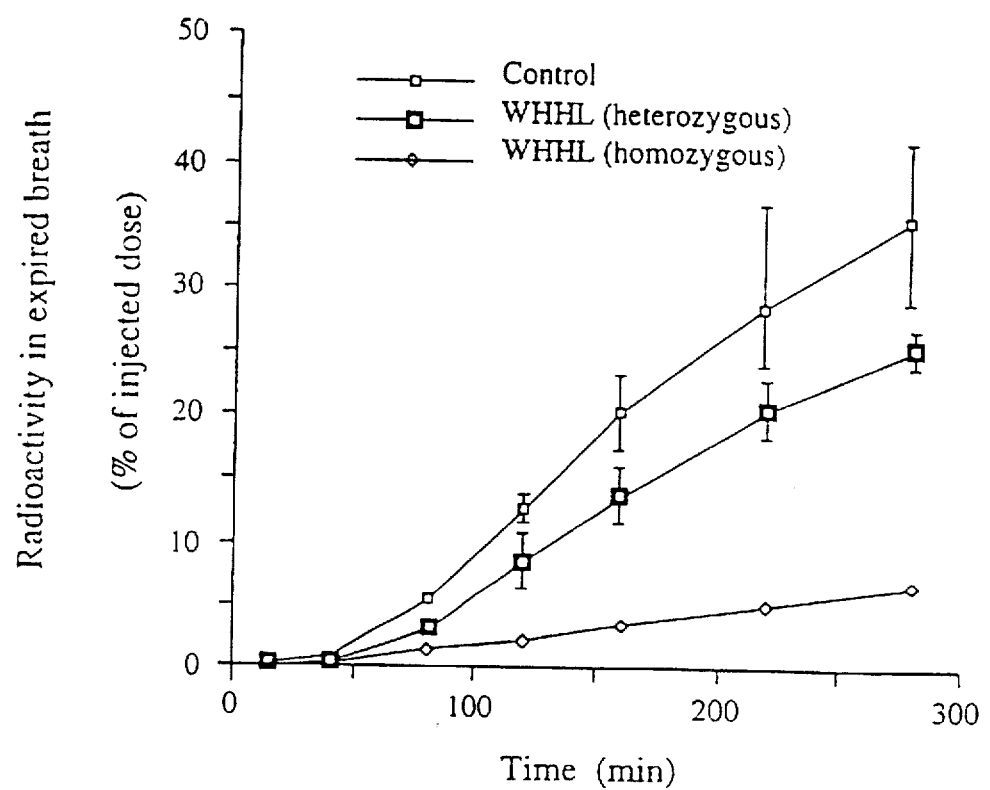
FIG. 3 shows a plot of "Radioactivity in expired breath" vs. "Time" as described in Example 3.

The radioactivity in expired breath in homozygous and heterozygous WHHL rabbits was compared with normal control rabbits. It is apparent from FIG. 3 that the rate of expiration of the radioactive $CO_2$ was much slower in the homozygous WHHL rabbits than in the control rabbits with normal low density lipoprotein receptors. In heterozygous WHHL animals, the appearance of radioactivity in expired breath was intermediate. The results are means±range from 2 rabbits in each group.

The diagnostic composition according to the invention is simple to administer according to the method of the invention and employs equipment already in place in most major diagnostic centres. The test yields precise quantitive information on the patients capacity or tolerance for metabolic handling of chyloremnants. The procedure is a great improvement in existing methods in terms of cost, patient intervention, and laboratory resources. Repeated measurements will be a valuable guide for assessment of the efficacy of the therapies or interventions at intervals of weeks or months. Studies of communities or populations will be useful in delineating genetic, environmental and cultural influences on chyloremnant tolerance. It will thus be appreciated that the diagnostic composition and method of using the same meet the objects of the invention.

We claim:

1. A labeled diagnostic composition for testing presence of or propensity for atherosclerosis and coronary artery disease comprising components which mimic essential features of an exogenous lipoprotein transport particle, said composition being capable of metabolisation by normal physiological pathways such that at least one labeled metabolite is detectable in the sampled blood or bodily waste of a patient being tested.

2. A labeled diagnostic composition as in claim 1 comprising components which mimic the essential features of a chyloremnant particle.

3. A labeled diagnostic composition as in claim 1 the metabolite of which is detectable in the expired breath of a patient being tested.

4. A method of determining the presence of or propensity for artherosclerosis or coronary artery disease in a patient requiring such determination comprising administering to said patient a labeled diagnostic composition which mimics essential features of an exogenous lipoprotein transport particle, and measuring the quantity of labeled metabolite in the bodily waste or blood of said patient so as to determine the quantity of labeled diagnostic composition metabolised by said patient.

5. A method as in claim 4 in which the labeled diagnostic composition mimics the essential features of a chyloremnant.

6. A method as in claim 4 wherein the bodily waste in which the level of composition metabolised is measured is the expired breath of said patient.

7. A labeled diagnostic composition as in claim 1 comprising a long chain fatty acid esterified to the cholesterol in the cholesteryl ester.

8. A labeled diagnostic composition as in claim 2 the metabolite of which is detectable in the expired breath of a patient being tested.

9. A labeled diagnostic composition as in claim 2 comprising a long chain fatty acid esterified to the cholesterol in the cholesteryl ester.

10. A labeled diagnostic composition as in claim 3 comprising a long chain fatty acid esterified to the cholesterol in the cholesteryl ester.

11. A labeled diagnostic composition as in claim 8 comprising a long chain fatty acid esterified to the cholesterol in the cholesteryl ester.

12. A method as in claim 5 wherein the bodily waste in which the level of composition metabolised is measured is the expired breath of said patient.

* * * * *